(12) United States Patent
Kang et al.

(10) Patent No.: US 9,814,370 B2
(45) Date of Patent: Nov. 14, 2017

(54) FILTER SWITCHING DEVICE FOR FLUORESCENCE ENDOSCOPIC TELEVISION CAMERA SYSTEM

(71) Applicant: KOREA ELECTROTECHNOLOGY RESEARCH INSTITUTE, Changwon-si, Gyeongsangnam-do (KR)

(72) Inventors: Uk Kang, Seoul (KR); Guang Hoon Kim, Busan (KR); Soo Jin Bae, Seoul (KR); Min Woong Jung, Seoul (KR); Garry V Papayan, St. Petersburg (RU); Vladimir Berezin, Ansan-si (KR)

(73) Assignee: KOREA ELECTROTECHNOLOGY RESEARCH INSTITUTE, Changwon-si (KR)

( * ) Notice: Subject to any disclaimer, the term of this patent is extended or adjusted under 35 U.S.C. 154(b) by 897 days.

(21) Appl. No.: 13/964,665

(22) Filed: Aug. 12, 2013

(65) Prior Publication Data

US 2014/0051925 A1 Feb. 20, 2014

(30) Foreign Application Priority Data

Aug. 17, 2012 (KR) ......................... 10-2012-0089906

(51) Int. Cl.
*A61B 1/06* (2006.01)
*A61B 1/00* (2006.01)
(Continued)

(52) U.S. Cl.
CPC .......... *A61B 1/00186* (2013.01); *A61B 1/043* (2013.01); *H04N 5/2251* (2013.01); *H04N 5/2254* (2013.01); *H04N 2005/2255* (2013.01)

(58) Field of Classification Search
CPC ... A61B 1/00186; A61B 1/043; A61B 1/0638; A61B 1/0015; G02B 23/2476;
(Continued)

(56) References Cited

U.S. PATENT DOCUMENTS 5,056,902 A 10/1991 Chinnock et al.
6,632,173 B1 * 10/2003 Kehr .................. A61B 1/00188
348/E5.027

(Continued)

*Primary Examiner* — Alexandra Newton
(74) *Attorney, Agent, or Firm* — Hauptman Ham, LLP

(57) ABSTRACT

The present invention relates to a filter switching device for a fluorescence endoscopic television camera system, and more particularly, to a filter switching device for a fluorescence endoscopic television camera system, which selectively transmits light to a detector sensor of a television camera according to the white light condition or the fluorescence condition to diagnose patients using a fluorescence endoscope. The present invention provides a filter switching device for a fluorescence endoscopic television camera system, which is configured to conveniently switch filters according to the rotational movement of the camera head, by inducing a change of magnetic forces according to the rotation of the camera head by magnetic substances disposed therein while maintaining a sealed structure inside the camera head connecting between a fluorescence endoscope and a television camera and thus allowing the frame of the camera head mounted with two types of filter to move upward and downward.

15 Claims, 7 Drawing Sheets

(51) Int. Cl.
*A61B 1/04* (2006.01)
*H04N 5/225* (2006.01)

(58) Field of Classification Search
CPC ...... G02B 26/008; G02B 7/006; G02B 21/16;
G02B 26/007; G02B 26/023; G02B 5/20;
H04N 5/2254; H04N 5/23209; G03B
11/00; G03B 17/12; G03B 17/14
USPC ....... 600/109–113, 160–180; 348/45, 65–76,
348/266–283; 359/234–236
See application file for complete search history.

(56) References Cited

U.S. PATENT DOCUMENTS

| | | | |
|---|---|---|---|
| 6,932,760 B1 | 8/2005 | Pang et al. | |
| 7,738,199 B1* | 6/2010 | Wen | G02B 7/006 |
| | | | 359/722 |
| 2010/0044607 A1* | 2/2010 | Miki | F16K 3/06 |
| | | | 251/129.11 |
| 2010/0268091 A1* | 10/2010 | Takaoka | A61B 1/0005 |
| | | | 600/478 |

\* cited by examiner

FILTER SWITCHING DEVICE FOR FLUORESCENCE ENDOSCOPIC TELEVISION CAMERA SYSTEM

CROSS-REFERENCE TO RELATED APPLICATION

This application claims under 35 U.S.C. §119(a) the benefit of Korean Patent Application No. 10-2012-0089906 filed Aug. 17, 2012, the entire contents of which are incorporated herein by reference.

BACKGROUND (a) Technical Field

The present invention relates to a filter switching device for a fluorescence endoscopic television camera system. More particularly, it relates to a filter switching device for a fluorescence endoscopic television camera system, which selectively transmits light to a detector sensor of a television camera according to the white light condition or the fluorescence condition to diagnose patients using a fluorescence endoscope.

(b) Background Art

Generally, a fluorescence endoscope has been used for the diagnosis of various diseases. The fluorescence endoscope enables the fluorescence observation of a target part of the body by irradiating excitation light on the target part while performing the functions of a typical endoscope for observing the surface of the internal parts of the body in detail.

For the diagnosis of patients using the fluorescence endoscope, a general reflection white light image reflected by the target part under the white light condition and a fluorescence image generated by the excitation light irradiated from the target part under the fluorescence condition are needed.

For this, a television camera with a high sensitive color chip is provided on the typical fluorescence endoscope so as to perform white light observation and fluorescence observation on the target part.

The television camera is provided with a detector sensor that is installed at one side of the television camera to implement the fluorescence image. The detector sensor of the television camera is connected to the fluorescence endoscope via a camera head so as to detect signal light delivered through the fluorescence endoscope.

In this case, the signal light incident under the white light condition and the fluorescence condition needs to be located on a signal light path before entering the detector sensor of the television camera such that light can be selectively transmitted to the detector sensor according to the white light condition and the fluorescence condition. Accordingly, a filter switching device needs to be provided in the camera head.

The television camera head connected to the external endoscope needs to have a small size, and have a sealed structure to maintain autoclaving. Also, the television camera head needs to have an ergonomic design and provide convenience for use.

Therefore, a filter switching device that can be installed in the camera head with a sealed structure and can conveniently replace a filter according to the while light or fluorescence condition upon diagnosis is needed.

Meanwhile, there are many prior documents about devices for moving optical parts in a camera head.

U.S. Pat. No. 6,932,760 discloses an autoclavable coupler for an endoscopic camera system. In this patent, when a focusing ring located outside a lens rider rotates, the rotating movement is changed into the straight movement by a screw and a groove located inside, and a lens holder with a lens is configured to move forward and backward between an endoscope and a CCD camera while being sealed.

Also, U.S. Pat. No. 5,056,902 discloses a magnetically coupled lens actuator. Unlike U.S. Pat. No. 6,932,760 described above, this patent is characterized in that a coupler is configured with a magnetic factor instead of a mechanical factor. That is, when an outermost tube rotates, a sleeve therein rotates to cause the rotating movement to be changed into the straight movement by a screw and a groove and cause the tube to move together with the movement of a cylindrical magnetic substance.

However, both above-mentioned patents are configured to allow a lens to move forward and backward in a sealed body to adjust the focus of the lens, and are not suitable for a filter switching device that needs a movement mechanism in which a filter can be located on the optical path and then be removed.

That is, both patents were developed such that lenses move forward and backward along the optical axis of the camera head in a sealed space using external rotating movement, while the optical filters need to be moved in a direction orthogonal to the optical axis to selectively implement the fluorescence and white light conditions. Accordingly, a device suitable for the filter replacement is needed.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a filter switching device for a fluorescence endoscopic television camera system, which is configured to conveniently replace a filter while maintaining a sealed structure inside a camera head connecting a fluorescence endoscope and a television camera.

In one aspect, the present invention provides a filter switching device for a fluorescence endoscopic television camera system, the device including: a frame including a first filter and a second filter disposed in a vertical direction; a frame guide for guiding a vertical movement of the frame; a pair of upper frame permanent magnets disposed at upper sides of the frame such that polarities thereof opposite to each other face the outside; a pair of lower frame permanent magnets disposed at lower sides of the frame vertically under the pair of the upper frame permanent magnets such that polarities thereof opposite to the polarities of the upper frame permanent magnets vertically over the lower frame permanent magnets face the outside while the polarities thereof opposite to each other face the outside; a rotating ring rotatably disposed outside the frame; a pair of first external permanent magnets disposed at one side of the rotating ring so as to face the pair of upper frame permanent magnets at a reference location, the pair of first external permanent magnets being disposed such that polarities thereof opposite to each other face the inside; and a pair of second external permanent magnets disposed at the other side of the rotating ring so as to face the pair of lower frame permanent magnets vertically under the pair of first external permanent magnets at the reference location, the pair of second external permanent magnets being disposed such that polarities thereof opposite to the polarities of the first external permanent magnets facing the second external permanent magnets based on the rotating ring face the inside, wherein as the polarities of the permanent magnets of the rotating ring facing the pair of upper frame permanent magnets and the pair of lower frame permanent magnets are changed by the rotation of the rotating ring, the frame moves upward and downward along the frame guide.

In an exemplary embodiment, a pair of first external permanent magnets may be disposed to generate an attractive force with the upper frame permanent magnets at the reference location, and a pair of second external permanent magnets may be disposed to generate a repulsive force with the lower frame permanent magnets at the reference location.

In another exemplary embodiment, the rotating ring may be disposed to be rotatable 180 degrees, and when the rotating ring rotates 180 degrees, the second external permanent magnets may generate a repulsive force with the upper frame permanent magnets and the first external permanent magnets may generate an attractive force with the lower frame permanent magnets.

In still another exemplary embodiment, the first external permanent magnets may be disposed to generate a repulsive force with the upper frame permanent magnets at the reference location, and the second external permanent magnets may be disposed to generate an attractive force with the lower frame permanent magnets at the reference location.

In yet another exemplary embodiment, the rotating ring may be disposed to be rotatable 180 degrees, and when the rotating ring rotates 180 degrees, the second external permanent magnets may generate an attractive force with the upper frame permanent magnets and the first external permanent magnets may generate a repulsive force with the lower frame permanent magnets.

In still yet another exemplary embodiment, the filter switching device may further include a capsule ring mounted with the frame guide. Here, the frame may be seated on one surface of the capsule ring so as to be movable upward and downward along the frame guide.

In a further exemplary embodiment, the capsule ring may have a window at the center thereof to form an optical path.

In another further exemplary embodiment, the filter switching device may further include a fixing plate that is fixed on the frame guide across the frame such that the frame does not move to a detector sensor.

In still another further exemplary embodiment, the filter switching device may further include a main holder connected to a detector sensor of a television camera and fixing the capsule ring.

In yet another further exemplary embodiment, the main holder may include a holder ring formed to receive the capsule ring, and the capsule ring may be fixed on an inner side of the holder ring.

In still yet another further exemplary embodiment, the rotating ring may be rotatably seated on an outer side of the holder ring.

In a still further exemplary embodiment, the holder ring may be provided with a pin facing the rotating ring, and the rotating ring may have a groove formed to receive the pin of the holder ring.

In a yet still further exemplary embodiment, the holder ring may be provided with at least one reference point indicating magnet, and the rotating ring may be provided with at least one start point setting magnet facing the reference point indicating magnet at the reference location.

In a yet still further exemplary embodiment, the rotating ring may be further provided with at least one end point setting magnet that is disposed to face the reference point indicating magnet when the rotating ring rotates.

In a yet still further exemplary embodiment, the filter switching device may further include a coupling ring fixed on an outer side of the rotating ring.

In a yet still further exemplary embodiment, the coupling ring may have a plurality of unevenness repeatedly formed along an outer circumference thereof.

In a yet still further exemplary embodiment, the coupling ring may be provided with two magnet markers toward the main holder, and the holder ring may be provided with a state selection sensor for detecting the magnet marker.

In a yet still further exemplary embodiment, the state selection sensor may detect the magnetic marker of the coupling ring to determine locations of the first filter and the second filter and transmit an electrical signal including information on a filter located on an optical path.

In a yet still further exemplary embodiment, the frame may be a rectangular frame, and the upper frame permanent magnets and the lower frame permanent magnets may be disposed at four corners of the rectangular frame.

In a yet still further exemplary embodiment, the first filter may be a fluorescence filter, and the second filter may be a white light filter.

In another aspect, the present invention provides a filter switching device for a fluorescence endoscopic television camera system, the device including: a frame including a first filter and a second filter disposed in a vertical direction; a frame guide for guiding a vertical movement of the frame; a pair of upper frame permanent magnets disposed at upper sides of the frame such that polarities thereof opposite to each other face the outside; a pair of lower frame permanent magnets disposed at lower sides of the frame vertically under the pair of the upper frame permanent magnets such that polarities thereof opposite to the polarities of the upper frame permanent magnets vertically over the lower frame permanent magnets face the outside while the polarities thereof opposite to each other face the outside; a rotating ring rotatably disposed outside the frame; three first external permanent magnets disposed at one side of the rotating ring at a uniform interval such that polarities thereof opposite to each other alternately face the inside; and three second external permanent magnets disposed at the other side of the rotating ring at a uniform interval such that polarities thereof opposite to the polarities of the first external permanent magnets facing the second external permanent magnets based on the rotating ring face the inside while the polarities thereof opposite to each other alternately face the inside, wherein at a reference location, two of the first external permanent magnets are disposed to face the pair of upper frame permanent magnets and two of the second external permanent magnets are disposed to face the pair of lower frame permanent magnets, and as the polarities of the permanent magnets of the rotating ring facing the pair of upper frame permanent magnets and the pair of lower frame permanent magnets are changed by the rotation of the rotating ring, the frame moves upward and downward along the frame guide.

In an exemplary embodiment, the two first external permanent magnets disposed to face the pair of upper frame permanent magnets may be disposed to generate an attractive force with the upper frame permanent magnets at the reference location, and the two second external permanent magnets disposed to face the pair of lower frame permanent magnets may be disposed to generate a repulsive force with the lower frame permanent magnets at the reference location.

In another exemplary embodiment, when polarities of the two first external permanent magnets and the two second external permanent magnets that face the pair of upper frame permanent magnets and the pair of lower frame permanent magnets, respectively, are changed by the rotation of the rotating ring, the two first external permanent magnets disposed to face the pair of upper frame permanent magnets may be disposed to generate a repulsive force with the upper frame permanent magnets, and the two second external permanent magnets disposed to face the pair of lower frame permanent magnets may be disposed to generate an attractive force with the lower frame permanent magnets.

In still another exemplary embodiment, the two first external permanent magnets disposed to face the pair of upper frame permanent magnets may be disposed to generate a repulsive force with the upper frame permanent magnets at the reference location, and the two second external permanent magnets disposed to face the pair of lower frame permanent magnets may be disposed to generate an attractive force with the lower frame permanent magnets at the reference location.

In yet another exemplary embodiment, when polarities of the two first external permanent magnets and the two second external permanent magnets that face the pair of upper frame permanent magnets and the pair of lower frame permanent magnets, respectively, are changed by the rotation of the rotating ring, the two first external permanent magnets disposed to face the pair of upper frame permanent magnets may be disposed to generate an attractive force with the upper frame permanent magnets, and the two second external permanent magnets disposed to face the pair of lower frame permanent magnets may be disposed to generate a repulsive force with the lower frame permanent magnets.

In still yet another exemplary embodiment, the filter switching device may further include a capsule ring mounted with the frame guide. Here, the frame may be seated on one surface of the capsule ring so as to be movable upward and downward along the frame guide.

In a further exemplary embodiment, the capsule ring may have a window at the center thereof to form an optical path.

In another further exemplary embodiment, the filter switching device may further include a fixing plate that is fixed on the frame guide across the frame such that the frame does not move to a detector sensor.

In still another further exemplary embodiment, the filter switching device may further include a main holder connected to a detector sensor of a television camera and fixing the capsule ring.

In yet another further exemplary embodiment, the main holder may include a holder ring formed to receive the capsule ring, and the capsule ring may be fixed on an inner side of the holder ring.

In still yet another further exemplary embodiment, the rotating ring may be rotatably seated on an outer side of the holder ring.

In a still further exemplary embodiment, the holder ring may be provided with a pin facing the rotating ring, and the rotating ring may have a groove formed to receive the pin of the holder ring.

In a yet still further exemplary embodiment, the holder ring may be provided with at least one reference point indicating magnet, and the rotating ring may be provided with at least one start point setting magnet facing the reference point indicating magnet at the reference location.

In a yet still further exemplary embodiment, the rotating ring may be further provided with at least one end point setting magnet that is disposed to face the reference point indicating magnet when the rotating ring rotates.

In a yet still further exemplary embodiment, the filter switching device may further include a coupling ring fixed on an outer side of the rotating ring.

In a yet still further exemplary embodiment, the coupling ring may have a plurality of unevenness repeatedly formed along an outer circumference thereof.

In a yet still further exemplary embodiment, the coupling ring may be provided with two magnet markers toward the main holder, and the holder ring may be provided with a state selection sensor for detecting the magnet marker.

In a yet still further exemplary embodiment, the state selection sensor may detect the magnetic marker of the coupling ring to determine locations of the first filter and the second filter and transmit an electrical signal including information on a filter located on an optical path.

In a yet still further exemplary embodiment, the frame may be a rectangular frame, and the upper frame permanent magnets and the lower frame permanent magnets may be disposed at four corners of the rectangular frame.

In a yet still further exemplary embodiment, the first filter may be a fluorescence filter, and the second filter may be a white light filter.

Other aspects and exemplary embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
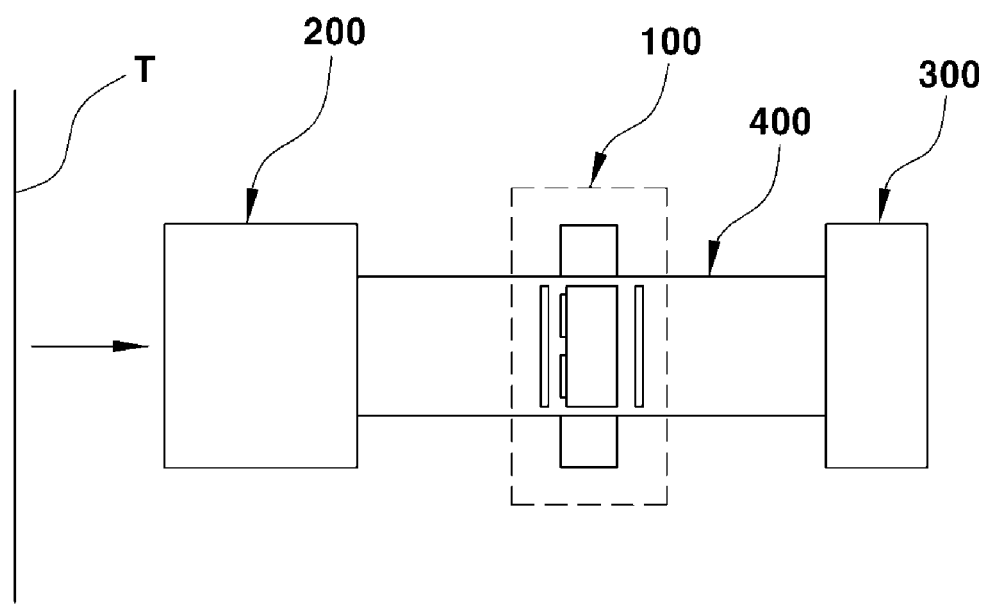
FIG. 1 is a view illustrating a filter switching device connected to a fluorescence endoscope and a detector sensor of a television camera according to an exemplary embodiment of the present invention.

Reference numerals set forth in the Drawings includes reference to the following elements as further discussed below:

| | |
|---|---|
| 100: filter switching device | 11: frame |
| 12: first filter | 13: second filter |
| 14, 15: upper frame permanent magnet | 16, 17: lower frame permanent magnet |
| 18: frame guide | 19: holder ring |
| 20: rotating ring | 21, 22: first external permanent magnet |
| 23, 24: second external permanent magnet | 31: frame |

-continued

Reference numerals set forth in the Drawings includes reference to the following elements as further discussed below:

| | |
|---|---|
| 32: first filter | 33: second filter |
| 34, 35: upper frame permanent magnet | 36, 37: lower frame permanent magnet |
| 38: frame guide | 39: holder ring |
| 40: rotating ring | 41, 42, 43: first external permanent magnet |
| 44, 45, 46: second external permanent magnet | 111: frame |
| 112: first filter | 113: second filter |
| 114, 115: upper frame permanent magnet | 116, 117: lower frame permanent magnet |
| 118: frame guide | 119: capsule ring |
| 120: fixing plate | 121: screw |
| 122: rotating ring | 123, 124, 125: first external permanent magnet |
| 126, 127, 128: second external permanent magnet | 129: groove |
| 130: start point setting magnet | 131: end point setting magnet |
| 132: main holder | 133: holder ring |
| 134: reference point indicating magnet | 135: pin |
| 136: state selection sensor | 137: coupling ring |
| 138: fixing member | 139: magnet marker |
| 140: sealing member | 200: fluorescence endoscope |
| 300: detector sensor | 400: camera head |
| : X: optical axis | T: target part |

It should be understood that the accompanying drawings are not necessarily to scale, presenting a somewhat simplified representation of various exemplary features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The above and other features of the invention are discussed infra.

The present invention relates to a filter switching device for a fluorescence endoscopic television camera system, which is configured to enable a user to conveniently replace two types of filter mounted in a camera head by rotating the surrounding of the camera head while maintaining a sealed structure inside the camera head in which a fluorescence endoscope and a television camera are connected.

Hereinafter, exemplary embodiments of a filter switching device for a fluorescence endoscopic television camera system will be described in detail with reference to the accompanying drawings.

FIG. 1 is a view illustrating a filter switching device connected to a fluorescence endoscope and a detector sensor of a television camera according to an exemplary embodiment of the present invention.

As shown in FIG. 1, a filter switching device 100 for a fluorescence endoscopic television camera system according to an embodiment of the present invention may be located between a fluorescence endoscope 200 for observing a target part T and a detector sensor 300 of a television camera for detecting a signal light delivered through the fluorescence endoscope.

That is, the fluorescence endoscope 200 and the detector sensor 300 may be connected by the camera head 400, and the camera head may be designed to have a sealed structure to maintain autoclaving.

Two filters may be disposed inside the sealed structure of the camera head 400 so as to filter signal light according to the white light or fluorescence condition. The two filters may be movably disposed so as to be selectively located on an optical axis X of the camera head 400.

Accordingly, the filter switching device may be configured to be disposed inside the camera head 400 with the sealed structure such that two filters can move upward and downward to select a white light filter or a fluorescence filter according to the manipulation of a user.

Figure 2:
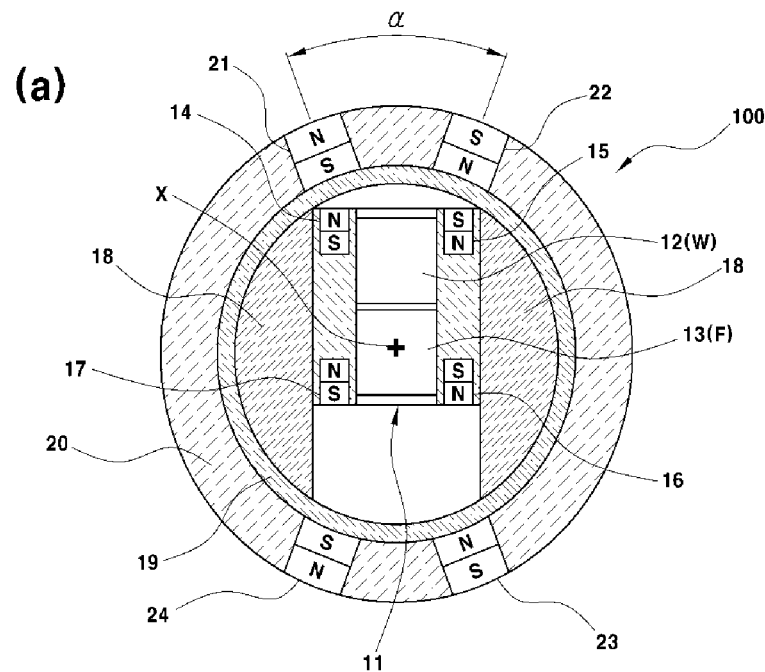
FIG. 2 is a view illustrating a schematic structure of a filter switching device for a fluorescence endoscopic television camera system and a process of replacing a filter according to an exemplary embodiment of the present invention.
Figure 2:
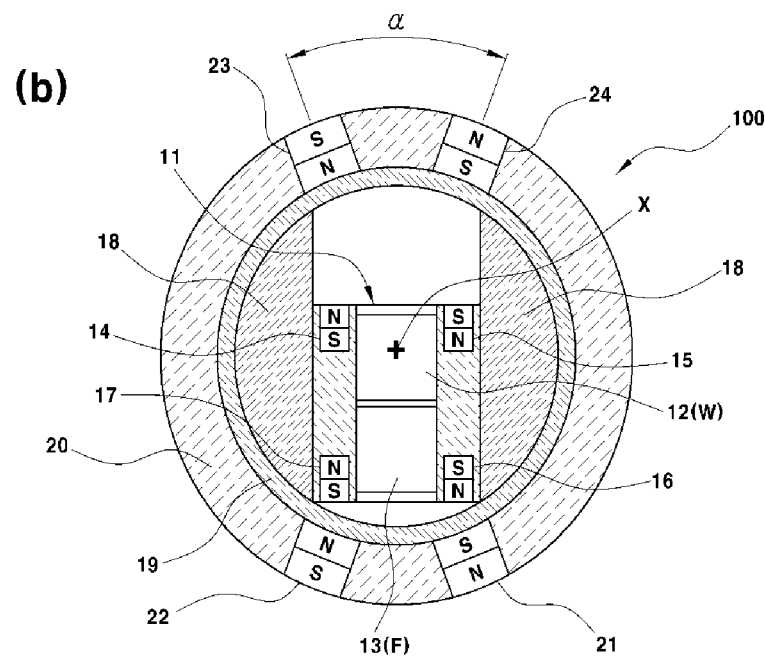
Figure 3:
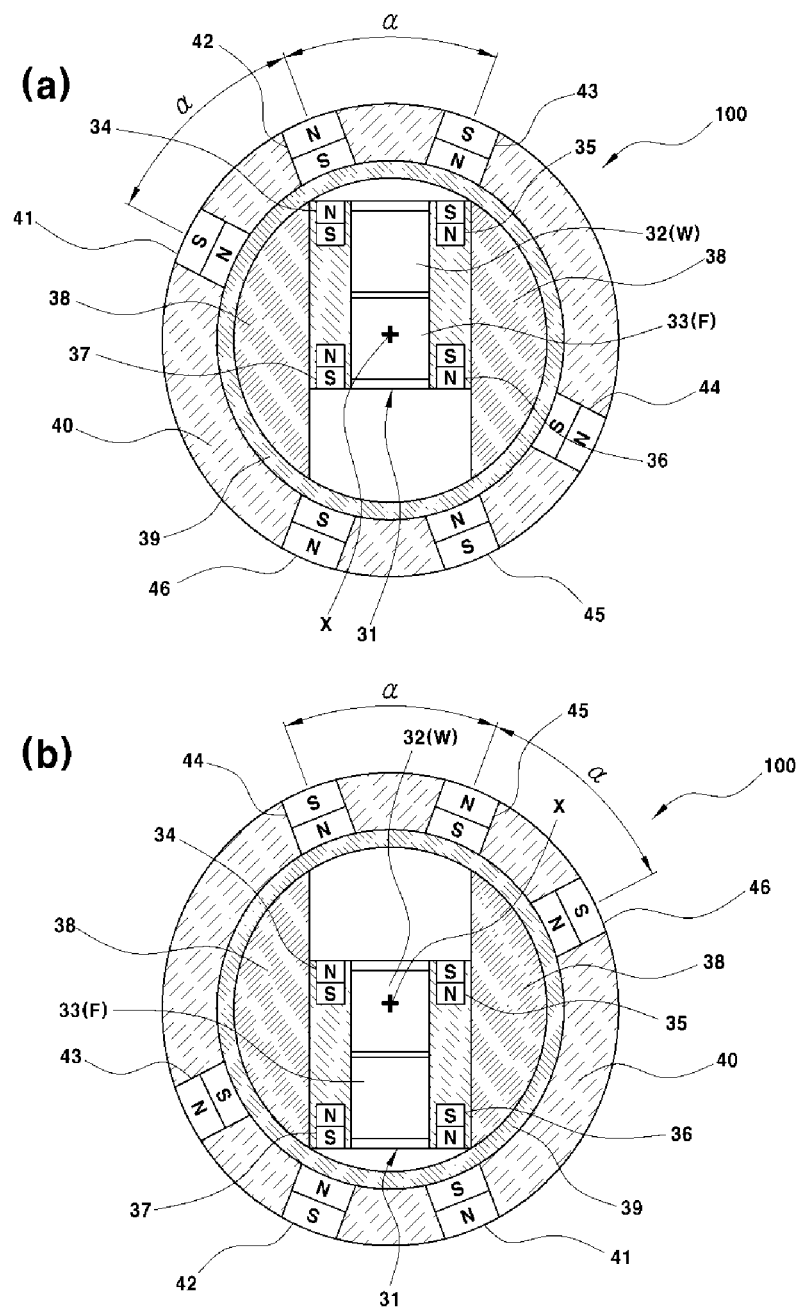
FIG. 3 is a view illustrating a schematic structure of a filter switching device for a fluorescence endoscopic television camera system and a process of replacing a filter according to another exemplary embodiment of the present invention.

FIGS. 2 and 3 are views illustrating schematic structures of a filter switching device for a fluorescence endoscopic television camera system and a process of replacing a filter according to exemplary embodiments of the present invention.

In this regard, FIGS. 2A and 3A illustrate filter switching devices in which fluorescence filters are positioned on the optical path from reference locations regarding each embodiment, and FIGS. 2B and 3B illustrate filter switching devices in which white light filters are positioned on the optical path according to the rotation of the rotating ring 20 from the condition of FIGS. 2A and 3A.

First, FIG. 2 illustrates a filter switching device for a fluorescence endoscopic television camera system, which is configured to enable a user to replace a filter by rotating the filter switching device by about 180 degrees from the reference location while holding a portion of the filter switching device.

In FIG. 2, a frame 11 equipped with two filters may be disposed to move upward and downward, and may be equipped with four permanent magnets. Also, a rotating ring 20 may be disposed outside the frame 11. The rotating ring 20 may be equipped with four permanent magnets at locations corresponding to the four permanent magnets equipped in the frame 11, allowing the eight magnets to face each other, respectively.

More specifically, a first filter 12 and a second filter 13 may be disposed at upper and lower sides of the frame 11 to filter light of different wavelengths. A frame guide 18 may be disposed at right and left side of the frame 11 to form a movement path for guiding the vertical movement of the frame 11.

Figure 6:
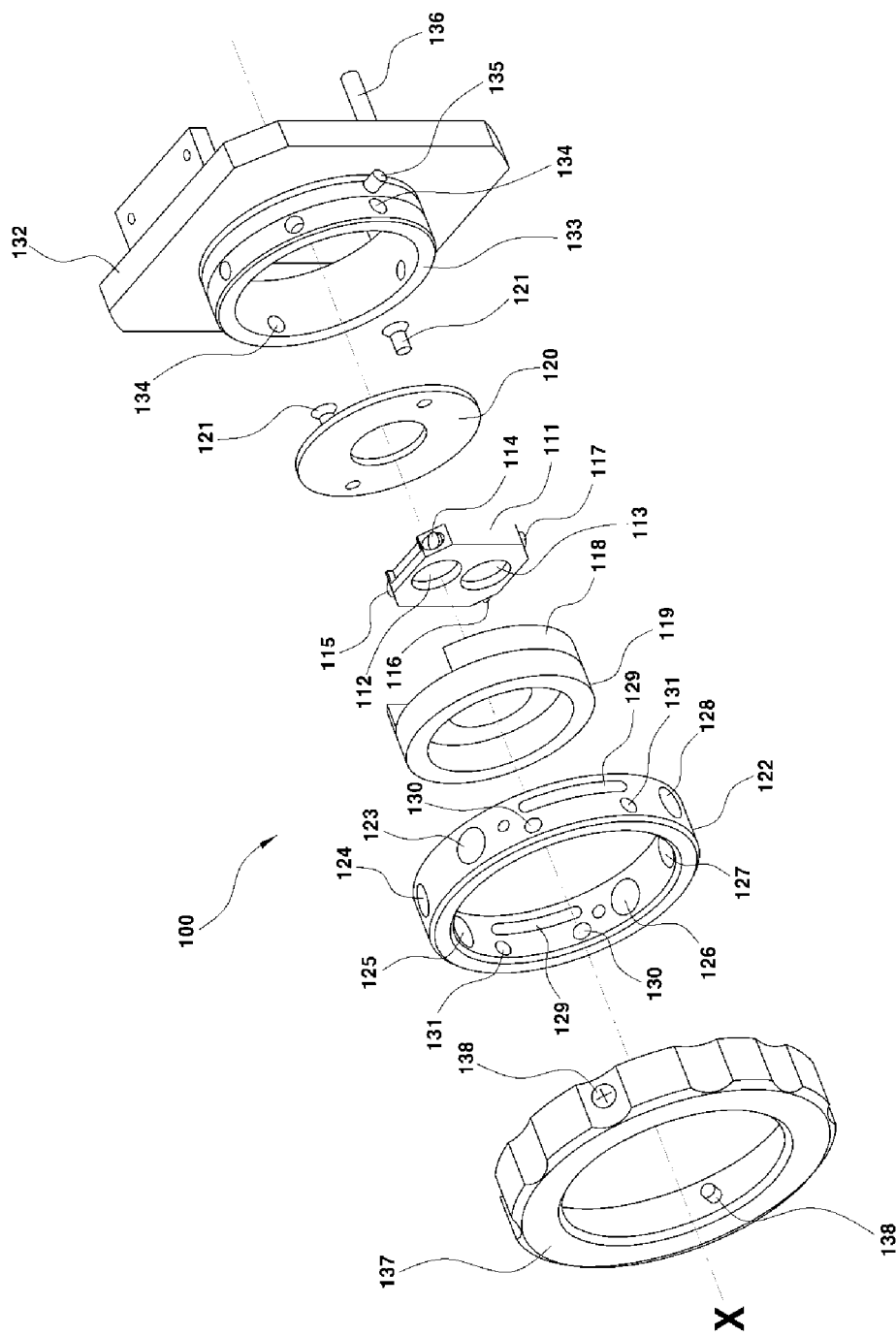
FIGS. 6 and 7 are exploded perspective views illustrating the filter switching device for the fluorescence endoscopic television camera system shown in FIGS. 4 and 5.

The frame guide 18, as shown in FIG. 6, may be mounted in a capsule ring 119 to secure the movement path of the frame 11. The capsule ring 119 may be fixed on a main holder 132 such that the frame 11 does not move except that the frame moves upward and downward.

In this case, the capsule ring 119 may be configured to be inserted into the holder ring 19 formed in the main holder 132, and may be configured to be mounted in the main holder 132 while the capsule ring 119 is inserted into the holder ring 19. Therefore, the frame guide 18 and the capsule ring 119 mounted in the main holder 132, as shown in FIGS. 2 and 6, may allow the frame 11 to be located over a space between one surface of the capsule ring 119 and the inner surface of the frame guide 18. The frame 11 may move along a path of an inner space guided by the frame guide 18 according to the magnetic force between the permanent magnets.

Also, the rotating ring 20 may be disposed outside the holder ring 19 formed on the main holder 132, and may be rotatable according to the manipulation of a user. The rotating ring 20 may be mounted with four permanent magnets that are magnetically linked with four permanent magnets disposed in the frame 11.

In this regard, FIGS. 2A and 2B illustrate the arrangement of the permanent magnets disposed in the frame 11 and the permanent magnets disposed in the rotating ring 20 according to their operation state.

More specifically, the four permanent magnets disposed in the frame 11 may be installed to generate an attractive force and a repulsive force in relation with the permanent magnets of the rotating ring 20 located outside.

As shown in FIG. 2, the four permanent magnets disposed in the frame 11 may include a pair of upper frame permanent magnets 14 and 15 disposed at the upper side of the frame 11 and a pair of lower frame permanent magnets 16 and 17 disposed at the lower side of the frame 11.

Also, the rotating ring 20 may be equipped with first external permanent magnets 21 and 22 and second external permanent magnets 23 and 24. The first external permanent magnets 21 and 22 and the second external permanent magnets 23 and 24 may be disposed to face the permanent magnets of the frame 11 at the reference locations.

In this case, the first external permanent magnets 21 and 22 and the second external permanent magnets 23 and 24 need to be symmetrically disposed at locations opposite to each other. In this case, when the rotating ring 20 rotates 180 degrees, the locations of the first external permanent magnets 21 and 22 and the second external permanent magnets 23 and 24 may be reversed, enabling the repeated operation of the frame.

Here, the reference location means the location of the rotating ring 20 when a specific filter is located on the optical axis X at the initial normal state of the filter switching device. As shown in FIG. 2A, the reference location means the location of the rotating ring 20 allowing the fluorescence filter to be located on the optical axis X.

Meanwhile, in the filter switching device for the fluorescence endoscopic television camera system, as a user rotates the outside structure of the camera head, the inside frame needs to be driven in a vertical direction by a magnetic force. For this, the filter switching device may be configured such that an attractive force and a repulsive force can be alternately generated at the upper part and lower part of the frame.

Accordingly, in an exemplary embodiment, as shown in FIGS. 2A and 2B, the pair of upper frame permanent magnets 14 and 15 may be disposed at the upper side of the frame 11 such that the polarities of the permanent magnets 14 and 15 opposite to each other face the outside, respectively. Also, the pair of lower frame permanent magnets 16 and 17 may be disposed at the lower side of the frame 11 in a vertically downward direction with respect to the pair of upper frame permanent magnets 14 and 15 such that the polarities of the permanent magnets 16 and 17 opposite to each other and opposite to the polarities of the permanent magnets 14 and 15 face the outside, respectively.

Also, the first and second external permanent magnets 21, 22, 23 and 24 that are disposed on the rotating ring 20 so as to face the pair of upper frame permanent magnets 14 and 15 or the pair of lower frame permanent magnets 16 and 17 at the reference location or the transformation location may be disposed to have polarities opposite to each other such that the magnetic force acting on the frame 11 can be changed into an attractive force or a repulsive force according to the rotation of the rotating ring 20.

That is, as shown in FIG. 2A illustrating a cross-sectional of the filter switching device at the reference location, the pair of first external permanent magnets 21 and 22 and the pair of second external permanent magnets 23 and 24 at the reference location are disposed to allow polarities opposite to each other to face the inside, respectively, and may be disposed so as to generate an attractive force or a repulsive force in relation with the upper frame permanent magnets 14 and 15 or the lower frame permanent magnets 16 and 17 of the frame 11.

At the reference location, an attractive force needs to act between the first external permanent magnets 21 and 22 and the upper frame permanent magnets 14 and 15, and a repulsive force needs to act between the second external permanent magnets 23 and 24 and the lower frame permanent magnets 16 and 17.

Accordingly, as shown in FIG. 2A, the two first external permanent magnets 21 and 22 need to be disposed to allow the opposite polarities to face the inside, the two second external permanent magnets 23 and 24 need also to be different opposite polarities to face the inside.

Furthermore, the second external permanent magnets 23 and 24 needs to be disposed to allow polarities opposite to those of the first external permanent magnets 21 and 22 opposite based on the center of the rotating ring 20 to face the inside.

Hereinafter, the operation process of the filter switching device for the fluorescence endoscopic television camera system will be described in detail with reference to FIGS. 2A and 2B.

First, at the reference location (a), the pair of first external permanent magnets 21 and 22 may be disposed to generate an attractive force with the upper frame permanent magnets 14 and 15, whereas the pair of second external permanent magnets 23 and 24 may be disposed to generate a repulsive force with the lower frame permanent magnets 16 and 17.

Also, when the rotating ring 20 rotates 180 degrees to be positioned at the transformation location (b), the second external permanent magnets 23 and 24 may be disposed to generate a repulsive force with the upper frame permanent magnets 14 and 15, and the first external permanent magnets 21 and 22 may be disposed to generate an attractive force with the lower frame permanent magnets 16 and 17.

Accordingly, as shown in FIGS. 2A and 2B, as a user rotates the rotating ring 20, the frame 11 may move upward or downward, allowing the first filter 12 or the second filter 13 to be selectively located on the optical axis X.

More specifically, as shown in FIG. 2A, at the reference location, since the pair of upper frame permanent magnets 14 and 15 faces the pair of first external permanent magnets 21 and 22 opposite thereto with opposite polarities, an attractive force may be generated between the permanent magnets opposite to each other. On the other hand, at the opposite side, since the pair of lower frame permanent magnets 16 and 17 faces the pair of second external permanent magnets 23 and 24 opposite thereto with the same polarity, a repulsive force may be generated between the permanent magnets. Therefore, at the reference location, an attractive force may be generated at the upper side of the frame 11 and a repulsive force may be generated at the lower side of the frame 11. Accordingly, at the reference location as shown in FIG. 2A, the frame 11 may be maintained at the upper side, and the fluorescence filter that is the second filter 13 mounted at the lower side of the frame 11 may be located on the optical axis X Accordingly, at the reference location as shown in FIG. 2A, a diagnosis may be performed under the fluorescence condition using the fluorescence filter.

On the other hand, FIG. 2B illustrates the filter switching device at the transformation location That is, when the rotating ring 20 rotates 180 degrees, the rotating ring 20 may be changed from the reference location to the transformation location while the frame 11 moves downward.

Here, the transformation location means the location of the rotating ring 20 when the filter switching occurs from the reference location. As shown in FIG. 2B, the transformation location denotes the location of the rotating ring 20 where the white light filter is located on the optical axis X.

Specifically, the first external permanent magnets 21 and 22 may moves to the lower side of the frame 11 according to the rotation of the rotating ring 20, whereas the second external permanent magnets 23 and 24 moves to the upper side of the frame 11.

In this reversed position, as the rotating ring 20 rotates 180 degrees, the first external permanent magnets 21 and 22 and the second external magnets 23 and 24 may be positioned at locations opposite to the reference location. Also, as the first and second external permanent magnets 21, 22, 23 and 24 move, the polarities of the permanent magnets of the rotating ring 20 facing the upper frame permanent magnets and the lower frame permanent magnets may be accordingly changed, respectively.

Accordingly, due to the change of the polarity, the upper frame permanent magnets may generate a repulsive force with the second external permanent magnet, and the lower frame permanent magnets may generate an attractive force with the first external permanent magnets 21 and 22 at the transformation location.

In FIG. 2, as the rotating ring rotates 180 degrees from the reference location (a), the polarity of the permanent magnets facing each other may be switched, and the frame 11 may move to the lower side like the reverted location (b).

Contrary to FIGS. 2A and 2B, the first external permanent magnets may be disposed to generate a repulsive force with the upper frame permanent magnets at the reference location, and the pair of second external permanent magnets may be disposed to generate an attractive force with the lower frame permanent magnets at the reference location. In this case, when the rotating ring rotates 180 degrees, the attractive force and the repulsive force may be switched to each other, allowing the frame 11 to move in the same manner.

FIGS. 3A and 3B illustrate a filter switching device for a fluorescence endoscopic television camera system according to another exemplary embodiment of the present invention. Three first external permanent magnets and three second external permanent magnets may be disposed in a rotating ring 40.

In the embodiment of FIG. 3, even though the rotating ring 40 rotates less than that of FIG. 2, the filter switching can be performed.

Specifically, the embodiment of FIG. 3 has a configuration similar to that of FIG. 2, except that three first external permanent magnets and three second external permanent magnets are disposed.

As shown in FIG. 3, three first external permanent magnets 41, 42 and 43 may include two first external permanent magnets 42 and 43 that are disposed at locations corresponding to upper frame permanent magnets 34 and 35 at the reference location. On the opposite side, three second external permanent magnets 44, 45 and 46 may be disposed to include two second external permanent magnets 45 and 46 that are disposed at locations corresponding to lower frame permanent magnets 36 and 37.

The first external permanent magnets 41, 42 and 43 and the second external permanent magnets 44, 45 and 46 may be disposed opposite to each other based on the central axis of the rotating ring 40, respectively, forming a symmetrical structure on the whole.

That is, as shown in FIGS. 3A and 3B, the permanent magnet 45 of the second external permanent magnets corresponding to the right permanent magnet 36 of the lower frame permanent magnets may be disposed at a location of the rotating ring 40 opposite to the permanent magnet 42 of the first external permanent magnets 41, 42 and 43 corresponding to the left permanent magnet 34 of the upper frame permanent magnets.

Therefore, although the rotating ring 40 rotates, the first external permanent magnets 41, 42 and 43 and the second external permanent magnets 44, 45 and 46 corresponding to each other may generate an attractive force or a repulsive force with the upper frame permanent magnets 34 and 35 or the lower frame permanent magnets 36 and 37 while maintaining their corresponding relation.

The first external permanent magnets 41, 42 and 43 and the second external permanent magnets 44, 45 and 46 may be disposed such that their polarities opposite to each other alternately face the inside to change the direction of the force acting on the frame 31 due to the change of the polarity according to the rotation of the rotating ring 40.

As shown in FIG. 3A, the first external permanent magnets 41, 42 and 43 may be disposed such that their polarities facing the inside can be disposed in clockwise order of N→S→N, and the second external permanent magnets 44, 45 and 46 may be disposed such that their polarities facing the inside can be disposed in clockwise order of S→N→S.

Accordingly, at the reference location, two of the first external permanent magnets 41, 42 and 43 may be disposed to face a pair of upper frame permanent magnets 34 and 35, and two of the second external permanent magnets 44, 45 and 46 may be disposed to face a pair of lower frame permanent magnets 36 and 37. On the other hand, since the polarities of the two first external permanent magnets and the two second external permanent magnets that face the pair of upper frame permanent magnets 34 and 35 and the pair of lower frame permanent magnets 36 and 37, respectively, are change due to the rotation of the rotating ring 40, the direction of forces that are acting may be changed, allowing the frame 31 to move upward and downward.

Also, the first external permanent magnets 41, 42 and 43 or the second external permanent magnets 44, 45 and 46 may be disposed at a uniform interval. Thus, a user may rotate the rotating ring 40 by a uniform angle to change the polarity of the permanent magnets acting on the frame 31 and allow the frame 31 to move upward and downward.

To describe the operation process in detail, FIG. 3A illustrates a filter switching device for a fluorescence endoscopic television camera system at the reference location. At the reference location, two first external permanent magnets 42 and 43 may generate an attractive force with the upper frame permanent magnets 34 and 35. Also, at the opposite side, two second external permanent magnets 45 and 46 may generate a repulsive force with the lower frame permanent magnets 36 and 37. Thus, the frame 31 may move to the upper side, allowing a lower fluorescence filter that is the second filter 33 among the two filters to be located on the optical axis X.

On the other hand, as shown in FIG. 3B, when the rotating ring 40 rotates by an action angle α corresponding to an angle between two first external permanent magnets from the reference location, the second external permanent magnets 44, 45 and 46 may be located at the transformation location.

That is, FIG. 3B is a result of rotating the rotating ring 40 of FIG. 3A by α°. Thus, as the rotating ring 40 rotates, the first external permanent magnets 41, 42 and 43 and the second external permanent magnets 44, 45 and 46 may also rotate α°. Since the polarities of the second external permanent magnets 44, 45 and 46 facing the upper frame permanent magnets 34 and 35 or the lower frame permanent magnets 36 and 37 are changed due to the rotation of the first external permanent magnets 41, 42 and 43 and the second external permanent magnets 44, 45 and 46, the attractive or repulsive force acting on the frame 31 may also be changed.

Accordingly, in FIG. 3B, since an attractive force is generated between the lower frame permanent magnets 36 and 37 and the second external permanent magnets 44, 45 and 46, and a repulsive force is generated between the upper frame permanent magnets 34 and 35 and the first external permanent magnets 41, 42 and 43, the frame 31 may move downward along the frame guide 38.

Accordingly, the while light condition in which the upper white filter, i.e., the first filter 32 among the two filters is located on the optical axis X may be achieved.

Contrary to FIGS. 3A and 3B, two permanent magnets of the first external permanent magnets 41, 42 and 43 may be disposed to generate a repulsive force with the upper frame permanent magnets 34 and 35 at the reference location, and two permanent magnets of the second external permanent magnets 44, 45 and 46 may be disposed to generate an attractive force with the lower frame permanent magnets 36 and 37 at the reference location. In this case, when the rotating ring 40 rotates α°, the attractive and repulsive forces may be switched, allowing the frame 31 to move upward and downward in the same manner.

Figure 4:
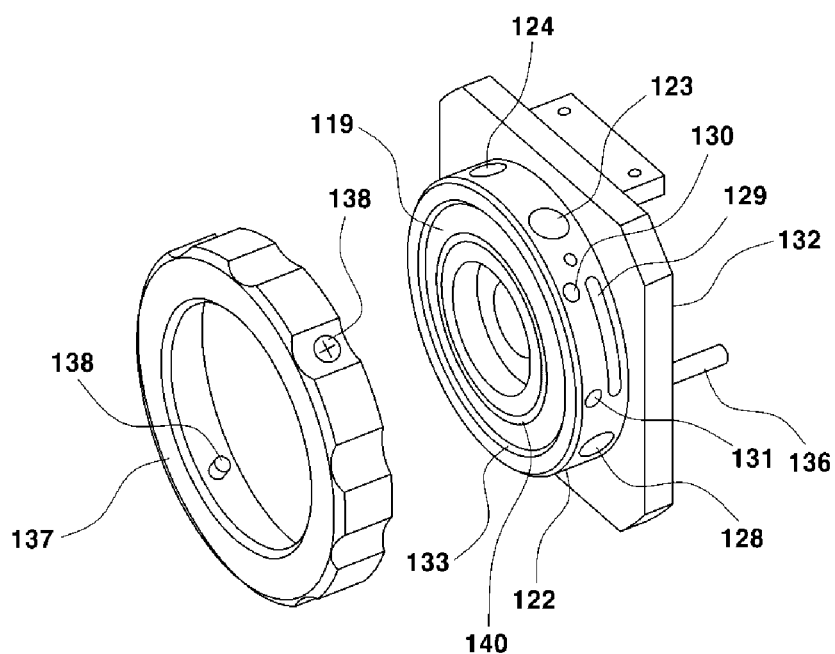
FIGS. 4 and 5 are front and rear perspective views illustrating a filter switching device for a fluorescence endoscopic television camera system according to an embodiment of the present invention.
Figure 5:
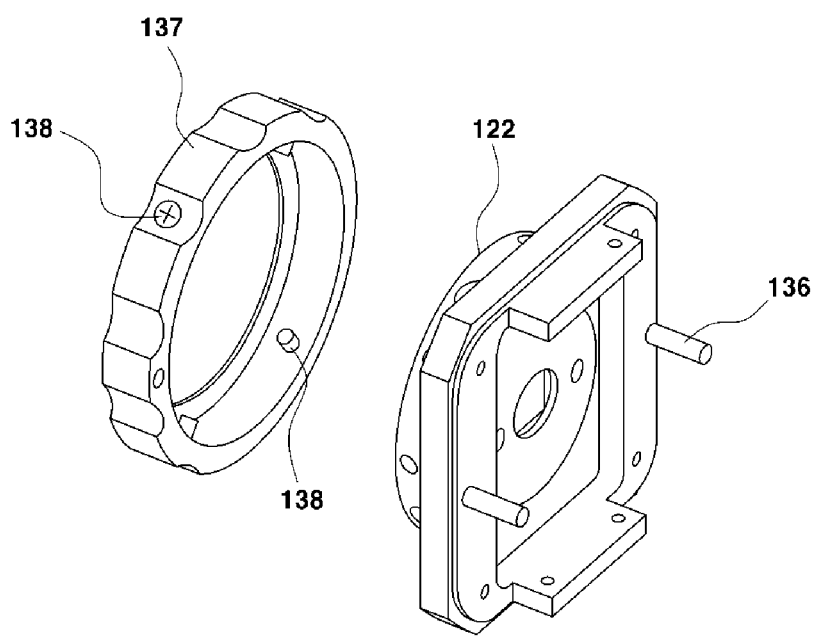
Figure 7:
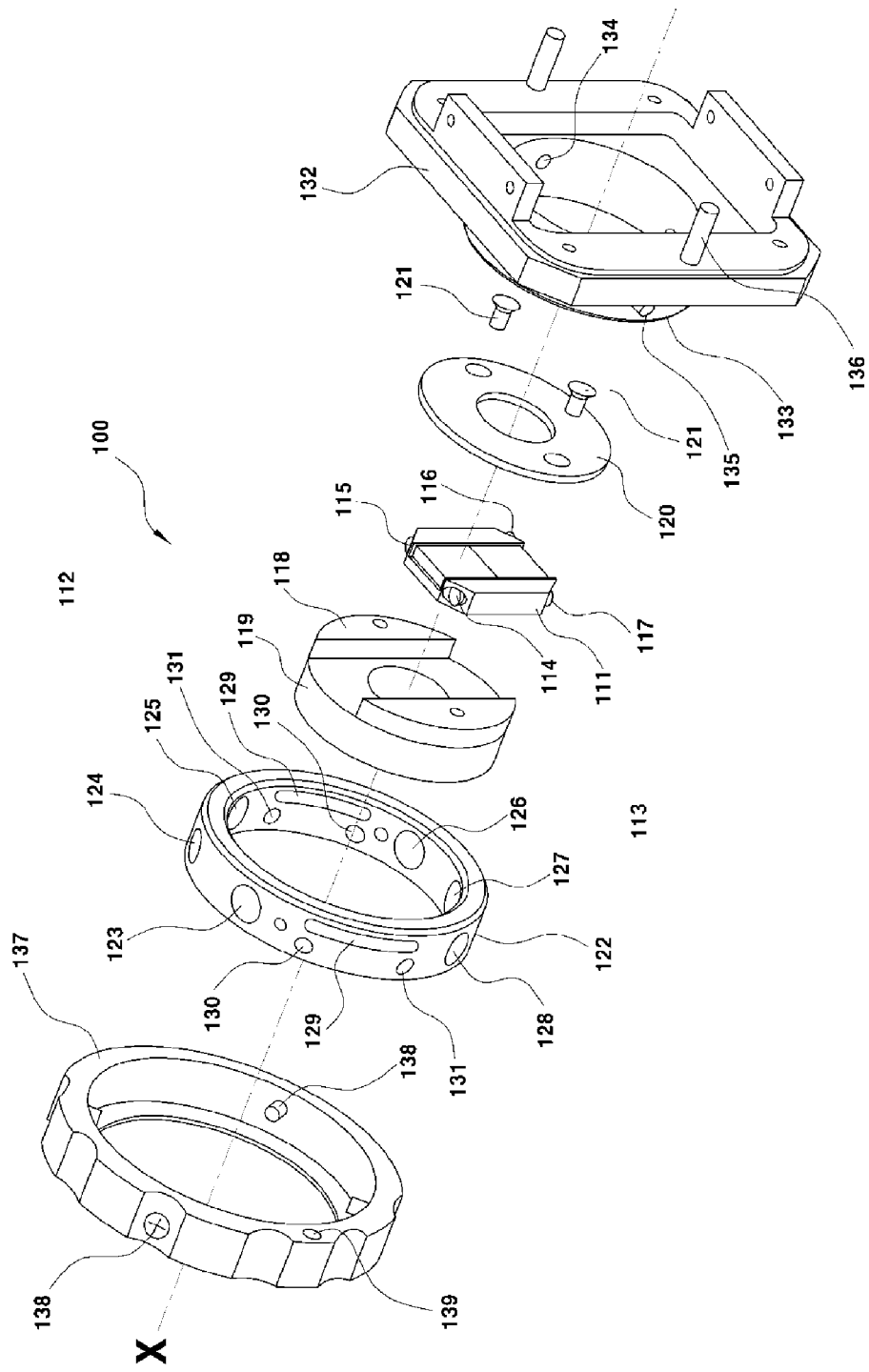

FIGS. 4 and 5 are front and rear perspective views illustrating a filter switching device for a fluorescence endoscopic television camera system according to an embodiment of the present invention. FIGS. 6 and 7 are exploded perspective views illustrating the filter switching device for the fluorescence endoscopic television camera system shown in FIGS. 4 and 5.

Referring to FIGS. 4 and 5, a filter switching module in which two filters and a plurality of permanent magnets are fixedly mounted in a main holder 132 may be coupled to a coupling ring 137 that is manufactured in such a way that a user can hold and rotate the coupling ring 137.

The coupling ring 137 may be coupled to the rotation ring 122 by a fixing member 138 such as bolt. When a user rotates the coupling ring 137, the rotating ring 122 may be moved by the fixing member 138. Thus, the filter switching process like FIGS. 3A and 3B may be performed.

Referring to FIGS. 6 and 7, two optical filters 112 and 113 may be fixedly disposed in the frame 111 that is movable and has a rectangular shape. Also, two upper frame permanent magnets 114 and 115 and two lower frame permanent magnets 116 and 117 may be disposed at the corners of the frame 11, respectively.

In this case, the filter, frame, and permanent magnets may be disposed at the inner side of the pair of frame guides 118 parallelly disposed on the capsule ring 119, and the frame 111 may be configured to freely move upward and downward in the frame guide 118.

Meanwhile, a fixing plate 120 may be disposed on the front side of the frame guide 118 to prevent the frame 111 from being separated toward the detector sensor of the television camera. The fixing plate 120 may be configured to be coupled to the frame 111 by a fixing member such as a screw 121. Also, although not shown, the fixing plate 120 may be fixed on the main holder 132, and thus, the frame 111 may be limited in movement of all directions except the vertical movement.

The capsule ring 119 may form a window to expose a filter on the optical axis X according to the movement of the frame 111, and may be fixedly inserted into the holder ring 133 on the main holder 132. As shown in FIG. 4, a sealing member 140 may be provided to seal between the capsule ring 119 and the holder ring 133, thereby completely sealing the inside of the filter switching device.

Meanwhile, the rotating ring 122 may be disposed outside the holder ring 133 to be rotatable with respect to the holder ring 133.

The rotating ring 122 may include first external permanent magnets 123, 124 and 125 and second external permanent magnets 126, 127 and 128 for generating a magnetic force with permanent magnets on the frame 111. The arrangement of the first external permanent magnets 123, 124 and 125 and the second external permanent magnets 126, 127 and 128 may be similar to that described above. In this embodiment, three first external permanent magnets 123, 124 and 125 and three second external permanent magnets 126, 127 and 128 may be disposed like that of FIG. 3. In FIGS. 6 and 7, three first and second external permanent magnets may be disposed, respectively.

As shown in FIGS. 6 and 7, a groove 129 may be formed on the side surface of the rotating ring 122 to set the path of the rotating ring 122 according to the action angle α to each permanent magnet. The groove 129 of the rotating ring 122 may be configured such that a pin 135 can move along the groove 129 by a predetermined action angle α while being fixed by the pin 135 formed on the holder ring 133.

Accordingly, the groove 129 may be configured such that the pin 135 is located at one end of the groove 129, that is, the pin 135 is located on the start point at the reference location. On the other hand, the groove 129 may be configured such that the pin 135 is located at the other end of the groove 129, that is, the pin 135 is located on the end point at the transformation location where the rotating ring 122 has rotated by the action angle α.

Therefore, the rotating ring 122 may be configured to rotate within a certain angle corresponding to the action angle by the pin 135 on the main holder 132 and the groove 129 in the rotating ring 122.

In FIGS. 6 and 7, a plurality of permanent magnets may be disposed on the rotating ring 122 and the holder ring 133 of the main holder 132 such that the start point and the end point regarding the rotation of the rotating ring 122 according to the reference location or transformation location can be verified.

Specifically, at least one reference point indicating magnet 134 may be disposed in the holder ring 133 to indicate the reference location, and at least one start point setting magnet 130 may be disposed in the rotating ring 122 to face the reference point indicating magnet 134 at the reference location.

Accordingly, at the reference location, since the rotating ring 122 is located at the start point within the rotation region, the start point setting magnet 130 disposed in the rotating ring 122 may become located on the reference point indicating magnet 134 disposed in the holder ring 133 to be fixed on the reference location by the attractive force between magnets.

Also, at least one end point setting magnet 131 may be further disposed in the rotating ring 122. The end point setting magnet 131 may be disposed to face the reference point indicating magnet 134 as the rotating ring 122 rotates.

Thus, when the rotating ring 122 is located at the transformation location due to the rotation of the camera head by a user, the end point setting magnet 131 disposed in the rotating ring 122 may become located on the reference point indicating magnet 134 disposed in the holder ring 133 to be fixed on the transformation location by the attractive force between magnets.

A coupling 137 may be disposed outside the rotating ring 122. The coupling may be fixed on the rotating ring 122 to move in linkage with the rotating ring 122. As a user holds and rotates the coupling ring 137, the coupling ring 137 may control the vertical movement of the frame 111 through the rotation of the rotating ring 122 therein. Preferably, the coupling ring 137 may have a plurality of unevennesses repeatedly formed along the outer circumference thereof to facilitate the rotation of the coupling ring 137 while a user hold the coupling ring 137.

As shown in FIG. 7, the coupling ring 137 may be provided with two magnet markers 139 facing the main holder 132. As shown in FIG. 6, the holder ring 133 may be provided with a state selection sensor 136 for detecting the magnet marker 139.

Since the state selection sensor 136 may detect whether or not the magnet marker 139 is located over the sensor, the state selection sensor 136 can detect the current location of the rotating ring 122 linked with the coupling ring 137 from the location of the magnet marker 139. Accordingly, the current filter condition according to the location of the frame 111 can be checked. One or more magnet markers 139 may be selectively disposed according to the reference location or the transformation location, and the state selection sensor 136 may be selectively disposed according to the installation location of the magnet marker 139.

In FIGS. 6 and 7, when all components are assembled, two magnet markers may be disposed at both sides of the coupling ring, and at the reference location, the magnet markers may be disposed at the front side of two state selection sensors, respectively.

The state selection sensor may be an enclosed knife switch operated by a magnet, enabling the detection of the magnet marker when the coupling ring rotates to be located on the state selection sensor.

Accordingly, the state selection sensor 136 may be configured to transmit electrical signals, that is, information on a filter currently located on the optical path, by determining the location of the first filter 112 or the second filter 113 according to the detection of the magnet marker 139. Accordingly, the electrical signal including information on the current filter condition may be transmitted to the endoscope or the television camera so as to achieve the device control according to the current filter condition.

In the filter switching device of the fluorescence endoscopic television camera system according to the embodiment of the present invention, all components except magnets are configured with non-magnetic substances for smooth operation.

As described above, a filter switching device for a fluorescence endoscopic television camera system according to an embodiment of the present invention has the following effects.

First, since a frame mounted with different filters is disposed in a camera head so as to move orthogonally to an optical axis, an effective diagnosis according to a while light condition and a fluorescence condition can be achieved.

Second, since the rotation movement of the camera head is converted into the vertical movement of the television camera filter, the television camera filter can be conveniently moved to a desired location.

Third, since the switching of the filter can be achieved even though the camera head is slightly rotated, the work is convenient.

Fourth, since the filters can be moved by magnetic forces between magnetic substances mounted in the camera head, a separate mechanical movement unit is not needed, thereby maintaining a sealed structure for autoclaving of the camera head.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A filter switching device for a fluorescence endoscopic television camera system, the filter switching device comprising:
   a frame comprising a first filter and a second filter disposed in a vertical direction;
   a frame guide for guiding a vertical movement of the frame;
   a pair of upper frame permanent magnets disposed at upper sides of the frame such that polarities thereof opposite to each other face the outside;
   a pair of lower frame permanent magnets disposed at lower sides of the frame vertically under the pair of the upper frame permanent magnets such that polarities thereof opposite to the polarities of the upper frame permanent magnets vertically over the lower frame permanent magnets face the outside while the polarities thereof opposite to each other face the outside;
   a rotating ring rotatably disposed outside the frame;
   a pair of first external permanent magnets disposed at one side of the rotating ring so as to face the pair of upper frame permanent magnets at a reference location, the pair of first external permanent magnets being disposed such that polarities thereof opposite to each other face the inside;
   a pair of second external permanent magnets disposed at the other side of the rotating ring so as to face the pair of lower frame permanent magnets vertically under the pair of first external permanent magnets at the reference location, the pair of second external permanent magnets being disposed such that polarities thereof opposite to the polarities of the first external permanent magnets facing the second external permanent magnets based on the rotating ring face the inside;
   a capsule ring mounted with the frame guide, wherein the frame is seated on one surface of the capsule ring so as to be movable upward and downward along the frame guide; and
   a main holder configured to be connected to a detector sensor of a television camera and fixing the capsule ring, wherein as the polarities of the permanent magnets of the rotating ring facing the pair of upper frame permanent magnets and the pair of lower frame permanent magnets are changed by the rotation of the rotating ring, the frame moves upward and downward along the frame guide, wherein the main holder comprises a holder ring formed to receive the capsule ring, and the capsule ring is fixed on an inner side of the holder ring, and wherein the rotating ring is rotatably seated on an outer side of the holder ring.

2. The filter switching device of claim 1, wherein the pair of first external permanent magnets are disposed to generate an attractive force with the upper frame permanent magnets at the reference location, and the pair of second external permanent magnets are disposed to generate a repulsive force with the lower frame permanent magnets at the reference location.

3. The filter switching device of claim 2, wherein the rotating ring is disposed to be rotatable 180 degrees, and when the rotating ring rotates 180 degrees, the second external permanent magnets generate a repulsive force with the upper frame permanent magnets and the first external permanent magnets generate an attractive force with the lower frame permanent magnets.

4. The filter switching device of claim 2, wherein the rotating ring is disposed to be rotatable 180 degrees, and when the rotating ring rotates 180 degrees, the second external permanent magnets generate an attractive force with the upper frame permanent magnets and the first external permanent magnets generate a repulsive force with the lower frame permanent magnets.

5. The filter switching device of claim 1, wherein the first external permanent magnets are disposed to generate a repulsive force with the upper frame permanent magnets at the reference location, and the second external permanent magnets are disposed to generate an attractive force with the lower frame permanent magnets at the reference location.

6. The filter switching device of claim 1, wherein the capsule ring has a window at the center thereof to form an optical path.

7. The filter switching device of claim 1, further comprising a fixing plate that is fixed on the frame guide across the frame such that the frame does not move to a detector sensor.

8. The filter switching device of claim 1, wherein the holder ring is provided with a pin facing the rotating ring, and the rotating ring has a groove formed to receive the pin of the holder ring.

9. The filter switching device of claim 1, wherein the frame is a rectangular frame, and the upper frame permanent magnets and the lower frame permanent magnets are disposed at four corners of the rectangular frame.

10. The filter switching device of claim 1, wherein the first filter is a fluorescence filter, and the second filter is a white light filter.

11. A filter switching device for a fluorescence endoscopic television camera system, the filter switching device comprising:

a frame comprising a first filter and a second filter disposed in a vertical direction;

a frame guide for guiding a vertical movement of the frame;

a pair of upper frame permanent magnets disposed at upper sides of the frame such that polarities thereof opposite to each other face the outside;

a pair of lower frame permanent magnets disposed at lower sides of the frame vertically under the pair of the upper frame permanent magnets such that polarities thereof opposite to the polarities of the upper frame permanent magnets vertically over the lower frame permanent magnets face the outside while the polarities thereof opposite to each other face the outside;

a rotating ring rotatably disposed outside the frame;

a pair of first external permanent magnets disposed at one side of the rotating ring so as to face the pair of upper frame permanent magnets at a reference location, the pair of first external permanent magnets being disposed such that polarities thereof opposite to each other face the inside;

a pair of second external permanent magnets disposed at the other side of the rotating ring so as to face the pair of lower frame permanent magnets vertically under the pair of first external permanent magnets at the reference location, the pair of second external permanent magnets being disposed such that polarities thereof opposite to the polarities of the first external permanent magnets facing the second external permanent magnets based on the rotating ring face the inside;

a capsule ring mounted with the frame guide, wherein the frame is seated on one surface of the capsule ring so as to be movable upward and downward along the frame guide; and a main holder configured to be connected to a detector sensor of a television camera and fixing the capsule ring, wherein as the polarities of the permanent magnets of the rotating ring facing the pair of upper frame permanent magnets and the pair of lower frame permanent magnets are changed by the rotation of the rotating ring, the frame moves upward and downward along the frame guide, wherein the main holder comprises a holder ring formed to receive the capsule ring, and the capsule ring is fixed on an inner side of the holder ring, and wherein the holder ring is provided with at least one reference point indicating magnet, and the rotating ring is provided with at least one start point setting magnet facing the reference point indicating magnet at the reference location.

12. The filter switching device of claim 11, wherein the rotating ring is further provided with at least one end point setting magnet that is disposed to face the reference point indicating magnet when the rotating ring rotates.

13. A filter switching device for a fluorescence endoscopic television camera system, the filter switching device comprising:

a frame comprising a first filter and a second filter disposed in a vertical direction;

a frame guide for guiding a vertical movement of the frame;

a pair of upper frame permanent magnets disposed at upper sides of the frame such that polarities thereof opposite to each other face the outside;

a pair of lower frame permanent magnets disposed at lower sides of the frame vertically under the pair of the upper frame permanent magnets such that polarities thereof opposite to the polarities of the upper frame permanent magnets vertically over the lower frame permanent magnets face the outside while the polarities thereof opposite to each other face the outside;

a rotating ring rotatably disposed outside the frame;

a pair of first external permanent magnets disposed at one side of the rotating ring so as to face the pair of upper frame permanent magnets at a reference location, the pair of first external permanent magnets being disposed such that polarities thereof opposite to each other face the inside;

a pair of second external permanent magnets disposed at the other side of the rotating ring so as to face the pair of lower frame permanent magnets vertically under the pair of first external permanent magnets at the reference location, the pair of second external permanent magnets being disposed such that polarities thereof opposite to the polarities of the first external permanent magnets facing the second external permanent magnets based on the rotating ring face the inside;

a capsule ring mounted with the frame guide, wherein the frame is seated on one surface of the capsule ring so as to be movable upward and downward along the frame guide;

a main holder configured to be connected to a detector sensor of a television camera and fixing the capsule ring; and a coupling ring fixed on an outer side of the rotating ring, wherein as the polarities of the permanent magnets of the rotating ring facing the pair of upper frame permanent magnets and the pair of lower frame permanent magnets are changed by the rotation of the rotating ring, the frame moves upward and downward along the frame guide, and wherein the coupling ring is provided with two magnet markers toward the main holder, and the holder ring is provided with a state selection sensor for detecting the magnet marker.

14. The filter switching device of claim 13, wherein the coupling ring has a plurality of unevenness repeatedly formed along an outer circumference thereof.

15. The filter switching device of claim 13, wherein the state selection sensor detects the magnetic marker of the coupling ring to determine locations of the first filter and the second filter and transmit an electrical signal comprising information on a filter located on an optical path.

* * * * *